(12) United States Patent
Li et al.

(10) Patent No.: US 7,029,907 B2
(45) Date of Patent: Apr. 18, 2006

(54) CELL CULTURE INCUBATING APPARATUS AND METHOD USING THE SAME

(75) Inventors: Wen-Tyng Li, Taipei (TW); Yu-Shi Weng, Pingtung (TW); Ming-Zheng Shiu, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/019,380

(22) Filed: Dec. 23, 2004

(65) Prior Publication Data
US 2005/0142656 A1 Jun. 30, 2005

(30) Foreign Application Priority Data
Dec. 26, 2003 (TW) ............................. 92137188 A (51) Int. Cl.
*C12M 1/12* (2006.01)
(52) U.S. Cl. .................. 435/297.1; 435/297.2; 435/305.1; 435/305.2
(58) Field of Classification Search ............ 435/297.1, 435/297.2, 305.1, 305.2
See application file for complete search history.

(56) References Cited

U.S. PATENT DOCUMENTS
2002/0072116 A1 6/2002 Bhatia et al.
2002/0173033 A1* 11/2002 Hammerick et al. ..... 435/305.2

FOREIGN PATENT DOCUMENTS
WO   WO 99/47922   9/1999

* cited by examiner

*Primary Examiner*—David A. Redding
(74) *Attorney, Agent, or Firm*—Bacon & Thomas, PLLC (57) ABSTRACT

A cell incubating apparatus and a method of culturing cells in vitro are disclosed, which relates to medical cell proliferation, pharmaceutical chemical screening and automatic cell analysis in tissue engineering technology. The apparatus establishes an imitating three-dimensional transportation microenvironment by assembling a top plate, a bottom plate and at least one culture plate apparatus for incubating cells. The apparatus is not only for incubating the tissue specific cells with biological function but also for lowering the cost of culturing cells for personal medical use.

19 Claims, 6 Drawing Sheets

CELL CULTURE INCUBATING APPARATUS AND METHOD USING THE SAME

BACKGROUND OF THE INVENTION

1. Field of the Invention

The invention is related to a cell incubating apparatus and the method of culturing cells in vitro, and especially, relates to a medical cell proliferation, pharmaceutical chemical screening and automatic cell analysis in tissue engineering technology.

2. Description of Related Art

In the field of tissue engineering, cell transplantation will play an important role in the future. Currently, the cell propagation apparatuses, which comprise not only for traditional laboratory cell incubating techniques but also for traditional bioreactors, have limitations for incubating a medical cell source. The shortcoming of the traditional laboratory cell incubating techniques mentioned above is the lack of a mass transporting system and difficult to display the real physiological activities ongoing inside the cell body. The bioreactor is only suitable in protein drug production as in, for example, the production volume of the stromal cells and fibroblasts with better tolerance for the above shortcoming. The bioreactor is excessively large and difficult to operate, has large fluidic shear force, lacks micro-environments similar to the physiological environment, and is impossible to incubate some tissue specific cells so far, for example, hepatocytes. Besides, using these bioreactors to produce personal cells is expensive; therefore, it is difficult industrializing cell production for personal cell therapy.

Massachusettes Institute of Technology and Massachusetts General Hospital in the United States disclosed a system containing micromatrix, an injection unit and sensors in WO9947922. The system is mainly used in pharmaceutical screening and analysis. However, even through the system illustrated above can maintain the cell function in vitro, the cells in the system forms a cell mass which is hard to isolate and expand. In the patent pended by University of California at San Diego, U.S. Pat. No. 20020072116, disclosed a nanoporous silicon bioreactor which is used for pharmaceutical screening such as analysis for the biological activity, metabolism, toxicity, mutagenicity or carcinogenicity of compounds. However, such a bioreactor is only for maintaining the function in vitro and not fit for cell proliferation.

Therefore, it is desirable to provide an improved method to mitigate the aforementioned problems.

SUMMARY OF THE INVENTION

The cell incubating apparatus of the present invention relates to a cell culture device that can establish an imitating three-dimensional mass transportation microenvironment, which assists the formation of cell cytokine gradient and the heterocellular reaction. The cell incubating apparatus is not only for incubating the tissue specific cells with biological function but also to lower the cost of cell production for personal medical treatment.

Another purpose of the present invention relates to a method of culturing cells in vitro. This method will establish an imitating three-dimensional transportation microenvironment, which assists to the formation of cell cytokine/chemokine gradient and the reactions between different types of cells. The cell incubating apparatus of the present invention is not only for incubating the tissue-specific cells with biological functions but also for lowering the cost of culturing cells for personal medication.

To achieve the purpose above, the cell incubating apparatus of the present invention, which cooperates with a fluid, comprises: a top plate having an input hole; a culture plate having a plurality of incubating units, a receiving part, and a plurality of fluid paths; and a bottom plate for collecting the fluid from the top plate and the culture plate. Among them, the incubating units and the fluid paths are located on the surface of the culture plate faced to the top plate. The fluid paths connect the incubating units and the receiving part. The receiving part overlaps the input hole of the top plate to receive the fluid from the input hole. An output hole is located in each incubating unit for draining away excessive fluid. Moreover, the culture plate is sandwiched between the top plate and the bottom plate as assembled, the fluid flows into the receiving part on the surface of the culture plate from the input hole of the top plate, passes along the fluid path then flows into each incubating unit, and arrives in the bottom plate from the output hole in each incubating unit.

The method of the present invention comprises following steps: (A) providing an apparatus comprising a top plate having an input hole; a culture plate having a plurality of incubating units, a receiving part, and a plurality of fluid paths; and a bottom plate for collecting the fluid form the top plate and the culture plate as illustrated above; (B) coating extracellular matrix or seeding stromal cells to cover the surface of the incubating unit; and (C) filling in a fluid into the input hole on the top plate, and the fluid flows to the bottom plate by passing the receiving part, the incubating units, the fluid paths, and the output hole of the culture plate.

Other objects, advantages, and novel features of the invention will become more apparent from the following detailed description when taken in conjunction with the accompanying drawings.

DETAILED DESCRIPTION OF THE PREFERRED EMBODIMENT

The present invention relates to a cell incubating apparatus preferably comprising a bottom plate, which is formed with a plurality of micro paths overlapping the output holes of each incubating unit on the culture plate for converging and collecting the fluid. More preferably, the bottom plate surface is provided with a collecting trough connected to the micro paths for collecting the fluid.

The invention of the incubating apparatus comprises, even more preferably, a transporting tract that connects to the collecting trough of the bottom plate and the input hole of the top plate for refluxing the fluid back to the input hole. Preferably, a spill hole and a through hole is formed on the top plate and the culture plate respectively, which is located at the relative location of collecting trough of the bottom plate, whereby the collecting trough connects to the through hole, the spill hole and the input hole on the top plate with the transporting tract.

The present invention discloses an incubating apparatus, wherein the top plate preferably comprises a plurality of apertures which overlap each incubating unit of the culture plate for testing the interaction between different cells, more preferably, a thin biologically compatible membrane is provided between the top plate and the culture plate as an interface for interaction between cells. The invention can optionally include at least one micro fluid path. The micro fluid path is formed in each incubating unit on culture plate to imitate blood capillaries between cells.

Depending on the requirements, the incubating units also can be seeded and covered by the stromal cells for facilitating the attachment of the cells. The material of the top plate, culture plate and bottom plate of the incubating apparatus of the present invention can be made of any traditional material with machinability. Preferably, the material of the top plate, culture plate and bottom plate are transparent material, more preferably, the material of the top plate, culture plate and bottom plate are acrylic, polycarbonate (PC) or polydimethylsiloxane (PDMS).

The present invention also relates to a method for incubating cells in vitro, which comprises, preferably, one transporting tract to connect the collecting trough and the input hole for refluxing the fluid back to input hole of the top plate. The method of incubating cells in vitro, more preferably comprises a plurality of apertures on the top plate, which overlap each incubating unit of the culture plate in order to analyze the interaction between different cells. More preferably, the apparatus used in the method of the present invention is provided with a biological membrane located between the apertures and the incubating units for providing an interface for cellular interaction. The invention relates to the method of incubating cells in vitro, which even more preferably comprises forming at least one micro fluid path on the incubating unit to imitate blood capillaries.

The materials of the top plate, culture plate and bottom plate included in the present method are preferably made of transparent material, and more preferably are made of acrylic polymers, PC or PDMS. The method of the present invention comprises preferably a step of using one illuminant on the incubating apparatus in order to observe the cellular activity.

Figure 1:
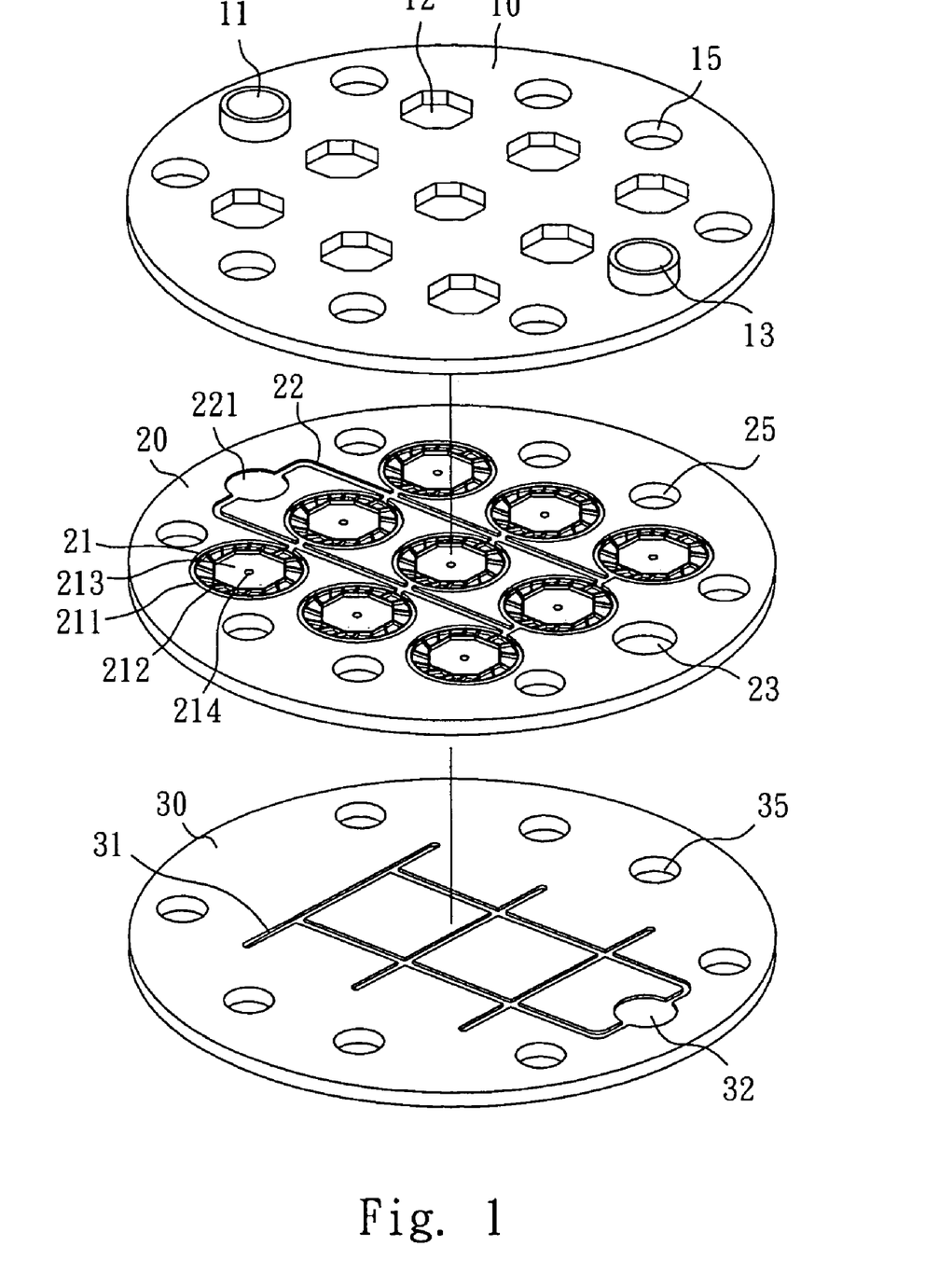
FIG. 1 is an exploded perspective view of the present invention relating to an incubating cell apparatus
Figure 2:
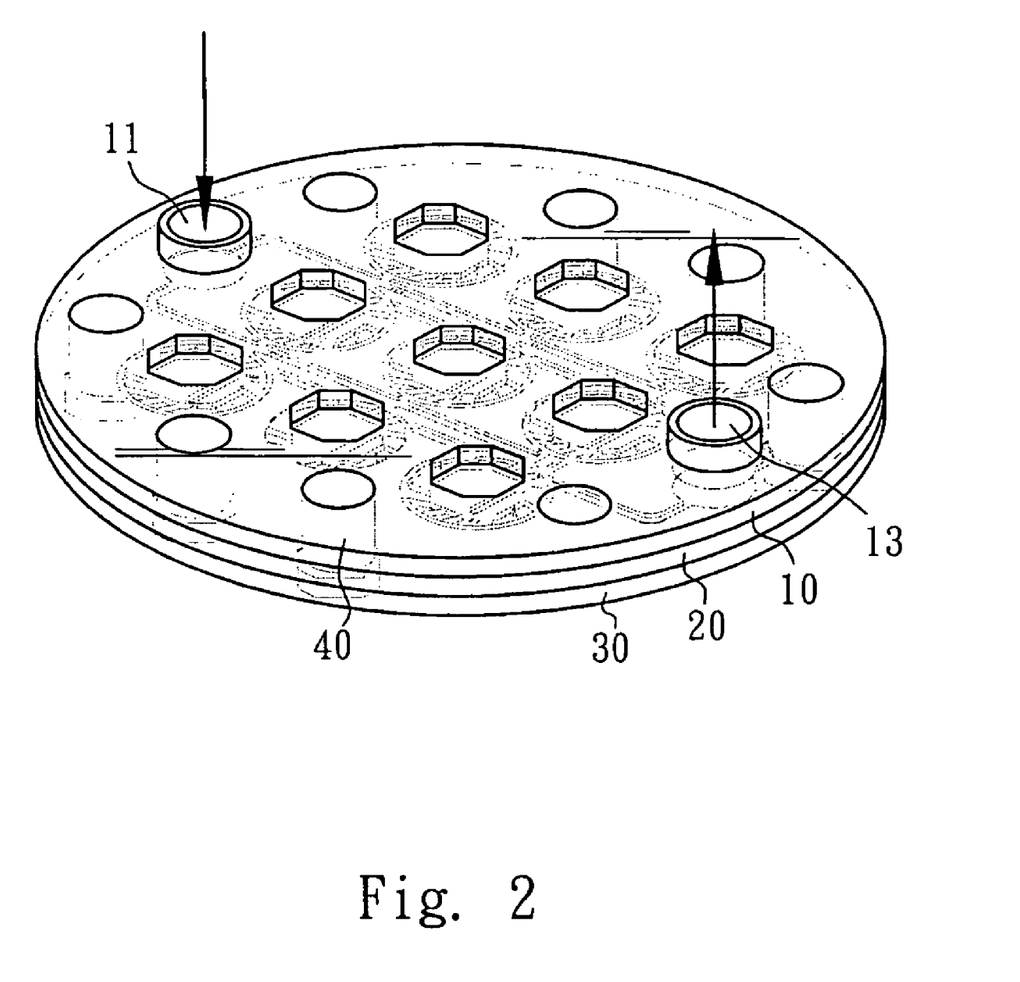
FIG. 2 is a perspective view of an assembly of the present invention relating to an incubating cell apparatus
Figure 5:
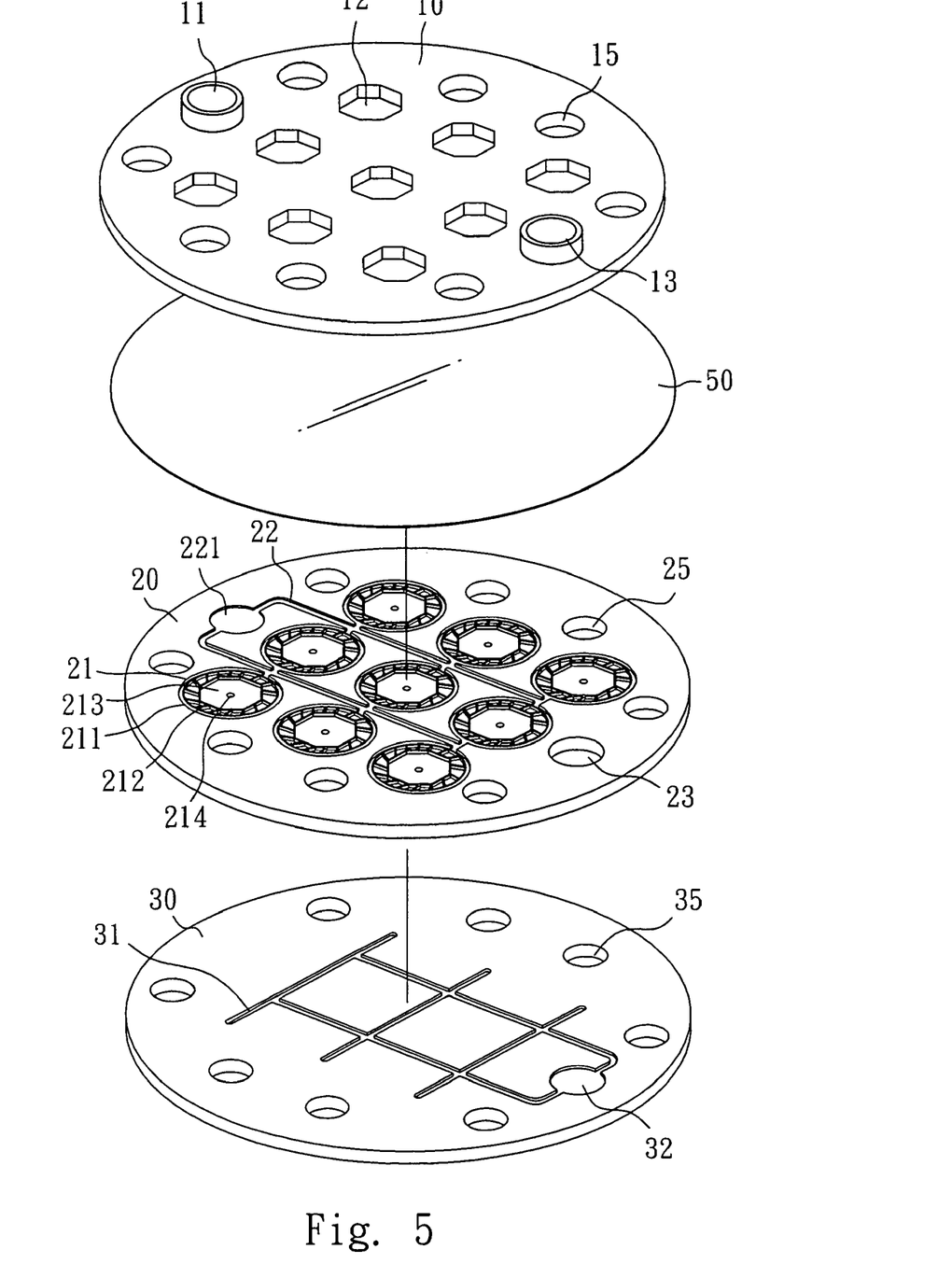
FIG. 5 is an exploded perspective view of another embodiment of the present invention wherein the incubating cell apparatus comprises a biological membrane.

With reference to FIGS. 1, 2 and 5, the invention of the cell incubating apparatus comprises a top plate 10, a culture plate 20 and a bottom plate 30. The culture plate 20 is sandwiched between the top plate 10 and the bottom plate 30.

The top plate 10, culture plate 20 and bottom plate 30 are respectively formed with screw holes 15, 25, and 35 in order to fasten them together using securing elements such as screws. The top plate 10 is provided with an input hole 11, a plurality of apertures 12 and a spill hole 13.

The surface of culture plate 20 is formed with a plurality of incubating units 21, a plurality of fluid paths 22, and a through hole 23. The fluid paths 22 are connected with each incubating unit 21. The fluid paths 22 are provided with a receiving part 221 to receive the fluid from the incubating apparatus and a fluid is injected into the receiving part 221 via the input hole 11.

Each incubating unit 21 comprises a circular hole 211 for separating the flowing. The circular hole 211 connects to a culture well 213 with a strike hole 212 and the culture well 213 is provided with an output hole 214. After the fluid is poured into the culture plate 20, the fluid passes through the output hole 214 and then directly flows down to the bottom plate 30. The culture well 213 on culture plate 20 overlaps the aperture 12 on the top plate 10.

Respective different cells in aperture 12 and culture well 213 are allowed to culture for testing heterocellular interaction. The culture plate also can be seeded or covered with a biological membrane 50 between the culture well 213 of the culture plate 20 and the aperture 12 of the top plate 10 to be an interface for cell interaction, as shown in FIG. 5.

The surface of bottom plate 30 is formed with a plurality of micro paths 31 overlapping the output hole 214 of the culture plate 20 and connects to a collecting trough 32 of the bottom plate 30. The output hole 214 connects with the micro path 31. The micro path 31 can converge the fluid from output hole 214 and collect in the collecting trough 32.

Figure 6:
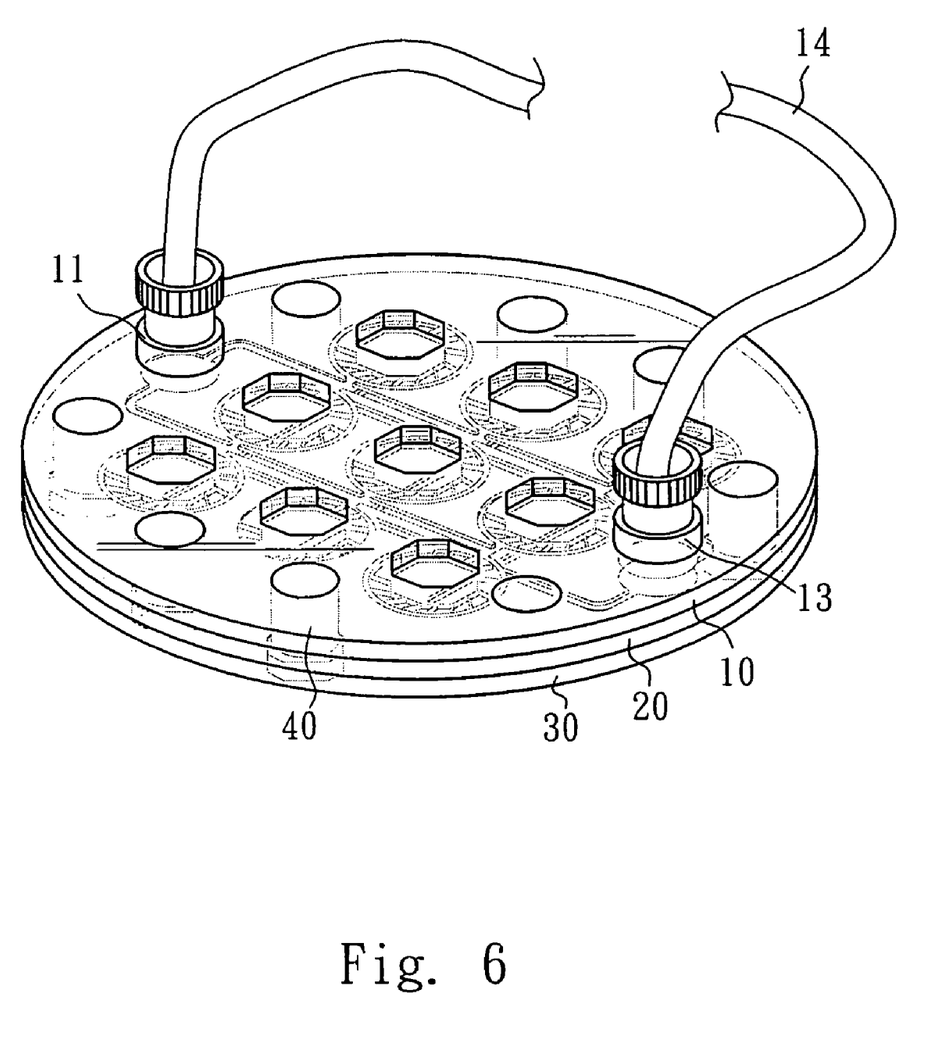
FIG. 6 is a perspective view of another embodiment of the present invention apparatus, which further comprises a transporting tract for the fluid collecting.

With reference to FIGS. 1, 2 and 6, the location of the collecting trough 32 aligns with the spill hole 13 on top plate 10 and the through hole 23 on the culture plate 20 when the apparatus of the present invention is assembled. By using a transporting tract 14 connects to the input hole 11, the spill hole, the through hole 23 and the collecting trough 32, the fluid can be collected from the collecting trough 32 of the bottom plate 30 into the input hole 11 of the top plate 10.

When performing the cell culture, the cells are loaded first. The cell incubating apparatus of the present invention is provided with several possible methods for cell loading, for example, the extracellular matrix is coated on the culture well 213 first and the cells are seeded. Cells are allowed to attach for 24 hours, then top plate 10, culture plate 20 and bottom plate 30 are assembled and secured with a screw 40 to form a cell incubating apparatus as shown in FIG. 2. After the apparatus has been assembled, a culture solution is filled from the input hole 11 into the top plate. The culture solution flows along the fluid path 22 and then respectively flows into the micro fluid path (not shown in all the figures), which is similar to capillaries, and the culture well 213.

After the culture plate 20 has been filled with the culture solution, the culture solution vertically flows down to the micro path 31 on the bottom plate 30 and then converges into the collecting trough 32 to form micro fluids that is similar to capillaries, in order to proceed the mass transfer, or build up the cell incubating apparatus first after coated with the extracellular matrix on each culture well 213, after which the filling procedure is begun. The cells circulate in the fluid paths to obtain a higher cell seeding density.

Then the flowing speed is reduced to zero, and wait for 4–6 hours, and then the filling procedure is carried out at low speed. After cells loading into the present invention of cell incubating apparatus as mentioned above, the filling procedure is started at different speeds and different compositions of each culture plate. After completion of a certain time period, for example, after 1, 2, 5 or 7 days, it can be observed by a microscope if there is any morphological changes occurred in cell structure.

As shown in FIGS. 3A~3D, HepG2 cells were cultured respectively in the present invention and a traditional cell incubating apparatus. The cell culture result of the traditional incubating apparatus with stationary culture technique shows some circular morphologies in FIG. 3C and FIG. 3D.

Figure 3:
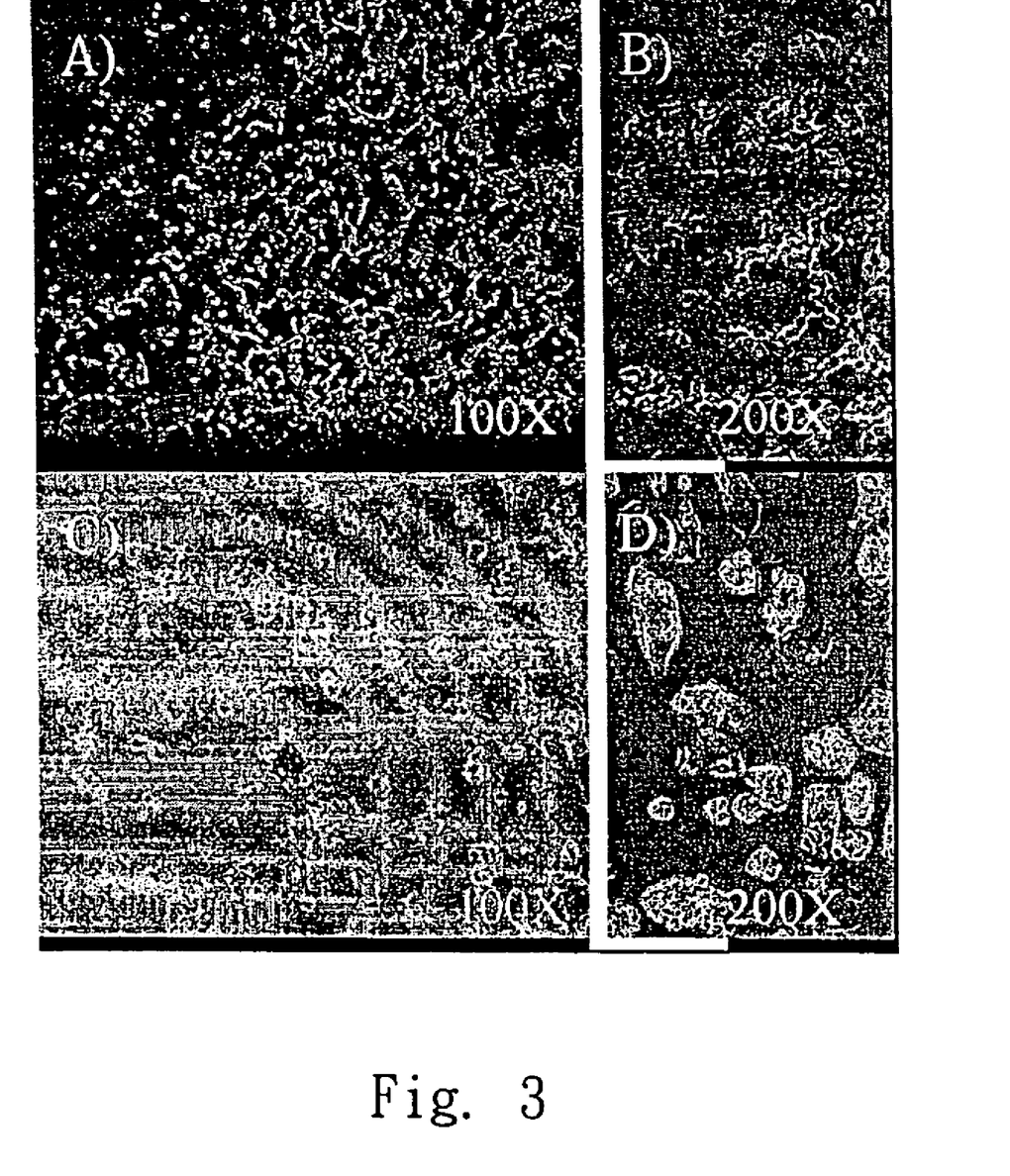
FIG. 3A and FIG. 3B are the morphology of HepG2 cells incubated in fluidic condition.
FIG. 3C and FIG. 3D are the morphology of HepG2 cells incubated in a static condition.

The cell incubating apparatus of the present invention displays an island shape of cell morphology after incubating and is also very similar to the physical cellular structure.

Figure 4:
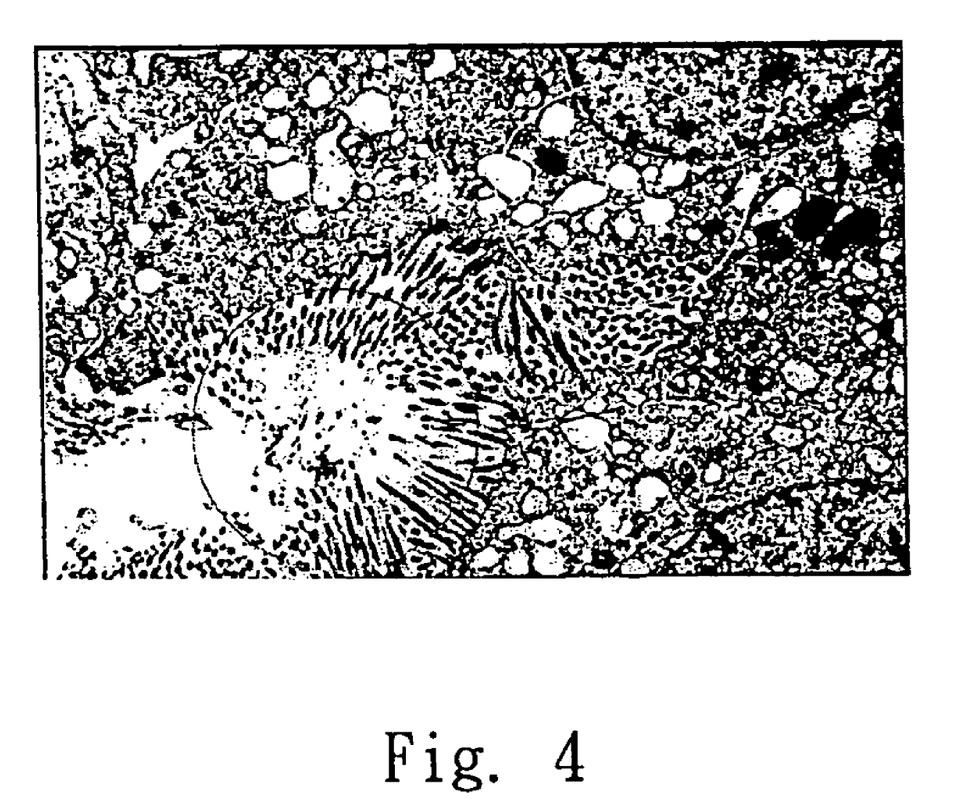
FIG. 4 is transimission electron microscope image of HepG2 cells cultured in fluidic setting. Microvilli formed have been observed.

FIG. 4 is a transmission electron microscopic graph of cells after undergoing the flowing incubating method of the present invention, wherein microvilli is located in the left bottom circle, and a tight junction is located in the right top circle. It is shown that the cultured cell structure contains microvilli and tight junctions, which are the specialized morphology of hepatic tissue. The result shows that the cell-culture environment supplied by the present invention can provide the ability of imitating real physical environment.

To perform the analysis procedures, for example, cytokines/chemokines in the system keep released from the cells under stimulations, the cell incubating apparatus of the present invention will transport the fluid from the collecting trough 32, pass through the through hole 23, spill hole 13 and transporting tract 14 to the transporting hole 11. Then the fluid will circulate in the path of the present invention mentioned above. In the meantime, for the preferable example, the material of top plate 10, culture plate 20 and bottom plate 30 are transparent PC.

The cell incubating apparatus of the present invention can be used for screening cellular activity by a photon detection system as illustrated by prior arts. On the other hand, the present invention is also provided with a plurality of culture plates between the top plate and the bottom plate; each culture plate can incubate the same or different types of cells. If the cells are the same, the cell incubating apparatus of the present invention can be used for cell proliferation. If the cells are different, the cell incubating apparatus of the present invention can be used for the observation of cell—cell interaction between the cells.

In reference to tissue engineering, the cell related products need to be highly personalized; the cell incubating apparatus of the present invention is also needed to combine with biomedical and scale-up technologies beneficial for marketing purpose. The present invention combines the cell physiology knowledge with industrialization purpose, and develops the new generation of bio-mimetic cells incubating system, which is provided with high specification, high density and also mimics the mass transportation system within cells, in order to apply in cell proliferation for medical, pharmaceutical chemical screening and automatic cell analysis.

The present invention relates to a novel technique in tissue engineering, which is applied with bio-mimetic techniques in a tissue-specific cell-simulating physiological system. The present invention is in an advantage of the 3D physical simulating system that can display the real cellular activity in vivo and also help to form cell cytokine/chemokine gradient and heterocellular interactions, in order to culture the tissue-specific cells for a delicate microenvironment. The cell incubating apparatus of the present invention can also reduce the cost of production, provide a manufacture process with an industrialized capability, and in addition can be designed for multiple productions, for disposable productions. The apparatus will proceed to manufacture the reaction system with low production cost and high additional value for future personal medical application.

Although the present invention has been explained in relation to its preferred embodiment, it is to be understood that many other possible modifications and variations can be made without departing from the spirit and scope of the invention as hereinafter claimed.

What is claimed is:

1. A cell incubating apparatus, which used with a fluid, comprising:
    a top plate having an input hole;
    a culture plate having a plurality of incubating units, a receiving part, and a plurality of fluid paths; wherein the incubating units and the fluid paths are located on at least one surface of the culture plate faced to said top plate, the fluid paths connect to each incubating unit, the receiving part overlapping the input hole of the top plate to receive the fluid from the input hole, and an output hole located in each incubating unit for draining away excessive fluid in the incubating unit; and
    a bottom plate for collecting the fluid from the top plate and the culture plate;
    wherein the culture plate is sandwiched between the top plate and the bottom plate as assembled, the fluid flows into the receiving part on the surface of the culture plate from the input hole of the top plate, passes along the fluid path then flows into each incubating unit, and arrives in the bottom plate from each output hole in the incubating units.

2. The cell incubating apparatus as claimed in claim 1, wherein the surface of bottom plate is provided with a plurality of micro paths which overlap the output hole in each incubating unit of the culture plate in order to converge or to collect the fluid from the incubating unit of the culture plate.

3. The cell incubating apparatus as claimed in claim 2, wherein the surface of bottom plate is provided with a collecting trough connected to a micro path for collecting the fluid.

4. The cell incubating apparatus as claimed in claim 3, further comprising a transport tract, which is connected to the collecting trough of the bottom plate and the input hole of the top plate in order to reflux the fluid in the collecting trough to the input hole.

5. The cell incubating apparatus as claimed in claim 4, wherein a spill hole and a through hole is formed or provided on the top plate and the culture plate respectively, and the transporting tract connects to the input hole, the spill hole-, the through hole on the culture plate, and the collecting trough on the bottom plate.

6. The cell incubating apparatus as claimed in claim 1, wherein the top plate further comprises a plurality of apertures which overlapping the incubating unit on the culture plate in order to analyze interaction in different cells.

7. The cell incubating apparatus as claimed in claim 6, further comprising a biological compatible membrane, which is located between the top plate and the incubating units of the culture plate.

8. The cell incubating apparatus as claimed in claim 1, further comprising at least one micro fluid path located on each incubating unit of said incubating plate to imitate blood capillaries between cells.

9. The cell incubating apparatus as claimed in claim 1, wherein the incubating unit is coated with an extracellular matrix to facilitate the attachment of the cells.

10. The incubating apparatus as claimed in claim 1, wherein the top plate, the culture plate and the bottom plate are transparent plates.

11. The incubating apparatus as claimed in claim 1, wherein the top plate, the culture plate and the bottom plate are made of acrylic, polycarbonate (PC) or polydimethylsiloxane (PDMS).

12. A method of incubating a cell in vitro, comprising following steps:

(A) providing a cell incubating apparatus which comprises:
   a top plate having an input hole;
   a culture plate having a plurality of incubating units, a receiving part, and a fluid path; wherein the incubating units and the fluid paths are located on at least one surface of the culture plate faced to said top plate, the fluid paths connect to the incubating units, the receiving part overlapping the input hole of the top plate to receive the fluid from the input hole, the output hole located in each incubating unit for draining away excessive fluid in the incubating unit; and
   a bottom plate for collecting the fluid from the top plate and the culture plate;
   wherein the culture plate is sandwiched between the top plate and the bottom plate as assembled, the fluid flows into the receiving part on the surface of the culture plate from the input hole of the top plate, passes along the fluid path then flows into each incubating unit, and arrives in the bottom plate from each output hole in the incubating units;
(B) coating extracellular matrix to cover the surface of the incubating unit; and
(C) filling in a fluid into the input hole on the top plate, and the fluid flows to the bottom plate by passing the receiving part, the incubating units, the fluid path, and the output hole of the incubating plate.

13. The cell incubating method as claimed in claim 12, wherein the bottom plate is provided with a collecting trough in order to collect the fluid.

14. The cell incubating method as claimed in claim 12, further comprising a transporting tract, which is connected to the collecting trough of the bottom plate and the input hole of the top plate for refluxing the fluid in the collecting trough to the input hole.

15. The cell incubating method as claimed in claim 12, further comprising a plurality of apertures on the top plate which overlapping the incubating units on the culture plate in order to analyze the interaction between different cells.

16. The cell incubating method as claimed in claim 15, further comprising a biological compatible membrane which is located between the aperture of the top plate and the incubating units of the culture plate in order to provide an interface for cell interactions.

17. The cell incubating method as claimed in claim 12, further comprising at least one micro fluid path located on each incubating unit of said incubating plate to imitate blood capillaries between cells.

18. The cell incubating method as claimed in claim 12, wherein the top plate, culture plate and bottom plate are transparent plates.

19. The cell incubating method as claimed in claim 18, further comprising photon detection system for the cell incubating apparatus in order to screen the activity of the cells.

* * * * *